United States Patent [19]

Kricka

[11] Patent Number: 5,306,621
[45] Date of Patent: Apr. 26, 1994

[54] ENHANCED CHEMILUMINESCENT ASSAY

[75] Inventor: Larry J. Kricka, Berwyn, Pa.

[73] Assignee: British Technology Group Limited, London, England

[21] Appl. No.: 844,598

[22] PCT Filed: Oct. 16, 1990

[86] PCT No.: PCT/GB90/01597
  § 371 Date: Apr. 1, 1992
  § 102(e) Date: Apr. 1, 1992

[87] PCT Pub. No.: WO91/05872
  PCT Pub. Date: May 2, 1991

[30] Foreign Application Priority Data

Oct. 17, 1989 [GB] United Kingdom ............ 8923344
May 14, 1990 [GB] United Kingdom ............ 9010763

[51] Int. Cl.$^5$ .............. G01N 21/76; G01N 33/53; C12Q 1/28; C12N 9/96
[52] U.S. Cl. .................. 435/7.91; 435/18; 435/21; 435/188; 435/28; 436/172
[58] Field of Search ............ 435/7.91, 18, 19, 21, 435/28, 966, 968, 188, 195; 436/172

[56] References Cited

U.S. PATENT DOCUMENTS 4,598,044 7/1986 Kricka et al. ............ 435/28
4,729,950 3/1988 Kricka et al. ............ 435/28

FOREIGN PATENT DOCUMENTS 25227 3/1981 European Pat. Off. .
27036 4/1981 European Pat. Off. .
49606 4/1982 European Pat. Off. .
116454 8/1984 European Pat. Off. .
296752 12/1988 European Pat. Off. .
317243 5/1989 European Pat. Off. .
8100725 3/1981 PCT Int'l Appl. .
8303140 9/1983 PCT Int'l Appl. .
8702667 5/1987 PCT Int'l Appl. .
2156518 10/1985 United Kingdom .
2192889 1/1987 United Kingdom .

OTHER PUBLICATIONS

P. D. Mize et al., Anal. Biochem. 179, 229-235 (1989).

Primary Examiner—Esther L. Kepplinger
Assistant Examiner—Nancy J. Parsons
Attorney, Agent, or Firm—Nixon & Vanderhye

[57] ABSTRACT

An enhanced chemiluminescent assay, in which a dihydrophthalazinedione such as luminol, a peroxidase such as HRP and an oxidant such as $H_2O_2$ are co-reacted in the presence of an enhancer such as p-iodophenol, is modified. The enhancer is generated by enzyme-catalysed reaction of a pro-enhancer, e.g. p-iodophenol phosphate is cleaved by alkaline phosphatase, enabling this enzyme to be assayed instead of peroxidase. Alternatively, the enhancer is added, an anti-enhancer such as p-nitrophenol is generated by enzymatic reaction of a pro-anti-enhancer such as p-nitrophenol phosphate and the reduction in luminescent emission is measured.

26 Claims, 2 Drawing Sheets

ENHANCED CHEMILUMINESCENT ASSAY

BACKGROUND OF THE INVENTION

1. Field of the Invention

The present invention relates to diagnostics, more specifically to the assay of enzyme activity, using a chemiluminescent reaction (a chemical reaction that results in the emission of light). The particular chemiluminescent reaction is that between a 2,3-dihydro-1,4-phthalazinedione (DPD), especially luminol or isoluminol, with an oxidant, especially hydrogen peroxide, and a peroxidase enzyme which catalyses the oxidation of the DPD by the oxidant. The oxidation is accompanied by the emission of light, thus generating a signal by which the enzyme activity can be assayed (detected or measured).

2. Description of the Prior Art

Enzymes are extensively used as labels in ligand-binder assays (e.g., immunoassay, DNA hybridization assay) and the signal amplification inherent in an enzyme catalyzed reaction confers great sensitivity on the assay. Chemiluminescent reactions are very sensitive and have been successfully used to measure enzyme activity with improvement in the detection limit for the enzyme over conventional enzyme assays L. J. Kricka, and T. P. Whitehead, Journal of Pharmaceutical and Biomedical Analysis, 5, 829-833 (1987).

Alkaline phosphatase can be measured chemiluminescently using the phosphate substrates disclosed in European Patent Application Publication No. 254051A and by Bronstein et al., Journal of Bioluminescence and Chemiluminescence, 4, 99-111, (1989). The enzyme cleaves the phosphate from the adamantly 1,2-dioxetane phosphate to produce a dephosphorylated intermediate which decomposes with the emission of light. A bioluminescent assay for this enzyme is also possible using firefly luciferin-O-phosphate (PCT Application Publication WO 87/02667). The enzyme cleaves the phosphate group and liberates firefly luciferin, which, unlike the luciferin phosphate, is a substrate in the bioluminescent reaction catalyzed by firefly luciferase:

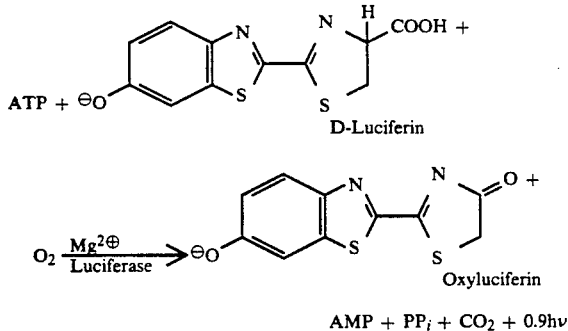

Peroxidase activity can be measured chemiluminescently using luminol as a substrate and the analytical utility of this reaction is significantly improved by the addition of certain enhancers, especially certain phenols, U.S. Pat. No. 4,598,044 and British Patent Application 2205945A or amines (U.S. Pat. No. 4,729,950), all owned by National Research Development Corporation.

It has been a problem that such enhanced chemiluminescent assays require the use of a peroxidase enzyme and are therefore primarily of use in assays in which the ligand or its binding partner are peroxidase-labelled. It would be desirable to have a chemiluminescent assay in which the ligand or binding partner can be labelled with a different enzyme, especially alkaline phosphatase.

Further prior art is mentioned after the "Summary of the invention", without which its context would not be clear.

SUMMARY OF THE INVENTION

The present invention is based on idea of using the phenolic enhancer of the above-mentioned existing peroxidase-based chemiluminescent assay to make the assay sensitive to the presence of a second enzyme. Pursuant to this idea, it has been found certain enzymes will catalyse reactions of certain non-enhancing or poorly-enhancing compounds, generating a good enhancer and thus allowing an enhanced peroxidase-catalyzed chemiluminescent reaction to proceed and, furthermore, that the light emission from this reaction is dependent on the enzyme used in the enhancer generation reaction. It has further been found that such assays can be performed as single tube assays in which the non-enhancing or poorly-enhancing compound is reacted with the enzyme in the presence of the reagents which give the chemiluminescent reaction.

The non-enhancing or poorly-enhancing compound is referred to herein as a "pro-enhancer". It will normally be a derivative of the enhancer and be cleavable by the action of the enzyme to yield the enhancer. Preferably it is a phosphate and the enzyme used to cleave it is an alkaline phosphatase.

It has also been found that certain "anti-enhancers" inhibit the effect of the enhancer on the chemiluminescent assay. For example para-nitrophenol inhibits the enhancing effect of para-iodophenol. Allowing a non-anti-enhancing compound to be acted on, conveniently cleaved by, an enzyme to generate the anti-enhancer is another way of making enhancement of the assay dependent on the enzyme. Thus, para-nitrophenol phosphate is cleaved by alkaline phosphatase to generate para-nitrophenol, thereby reducing the light emission from a DPD-oxidant-peroxidase-phenolic enhancer chemiluminescent reaction mixture. The non-anti-enhancer, or poorly-acting anti-enhancer, which normally is a derivative of the anti-enhancer, is herein termed a "pro-anti-enhancer". The term "anti-enhancer" is preferred to "inhibitor", as it is only necessary for the compound to cancel at least part of the enhancement. It need not and preferably should not inhibit the unenhanced chemiluminescent reaction.

Accordingly the present invention provides a method of chemiluminescent assay in which a chemiluminescent reaction takes place between a peroxidase, an oxidant and a dihydrophthalazinedione (DPD), in the presence of an enhancer, and in which a substance which enables said reaction to take place is detected or measured luminescently, characterised in that the enhancer is generated by the enzyme-catalysed reaction of a pro-enhancer or an enhancer is already present and an anti-enhancer which at least partly inhibits the enhancement is generated by enzyme-catalysed reaction of a pro-anti-enhancer, and in that the enhancer or anti-enhancer generation-catalysing enzyme (in free or bound form) or a substance dependent on said enzyme is assayed.

The invention also includes a kit for carrying out an assay in which a chemiluminescent reaction takes place between a peroxidase, an oxidant and a dihydrophthalazinedione (DPD), in the presence of an enhancer, said kit including said DPD, characterised in that the kit further comprises either (a) a pro-enhancer from which an enhancer can be generated by an enzyme-catalysed reaction or (b)(i) an enhancer and (ii) a pro-antienhancer from which an anti-enhancer which at least partly inhibits the enhancement, can be generated by an enzyme-catalysed reaction.

ADDITIONAL PRIOR ART

The detection limit for an enzyme can be significantly improved by means of a coupled assay protocol in which the enzyme to be measured converts a substrate to a product which activates a second enzyme which then converts a substrate to a measurable product. The increased sensitivity of this type of assay is due to the cumulative effect of successive enzymatic amplification steps.

UK Patent Application Publication No. 2156518A and its divisional 2192889A (London Biotechnology Ltd.) disclose the use of a prosthetogen. The enzyme acts on the prosthetogen (an inactive form of a cofactor or a prosthetic group) to produce a product which is ultimately detected. The prosthetogen has the formula R-X where R is a pyrimidine 3'-phosphate residue and X is a cleaving group linked through R to the phosphate group, e.g. riboflavin. The recognition system produces the enzyme ribonuclease A which cleaves the R-X bond, liberating a compound X-OH (riboflavin). The riboflavin is acted on by riboflavin kinase to produce flavin mononucleotide (FMN), which undergoes further reactions for detection.

European Patent Application Publication 27036A (C. H. Self) describes a coupled assay protocol in which the enzyme produces or removes a modulator of a second enzyme. The modulator can be an activator, inhibitor, substrate, cofactor, coenzyme, or a metal ion.

PCT Application Publication No. WO 81/00725 (P. Duffy and The Prince Charles Hospital Development Centre Trust) describes another complicated system, which can be exemplified as follows. The ligand to be detected, digoxin, competes with enzyme-conjugated digoxin for anti-digoxin antibody. The enzyme is beta-galactosidase. To detect the free or bound conjugate, the beta-galactosidase is reacted with a phenol beta-galactoside substrate which produces phenol. The phenol product is amplified by reacting it with tyrosinase to produce ortho-quinone, which is reduced to o-catechol by the oxidation of NADH to NAD.

In European Patent Application Publication No. 49606A (C. H. Self) the amplification system is illustrated as follows. Creatine kinase is detected by its reaction with creatine phosphate to give ATP. The ATP, described as the "activator", is used to drive the reaction of fructose 6-phosphate to fructose diphosphate, catalysed by the enzyme fructosphosphokinase, with conversion of the ATP to ADP. The ADP is then used to drive a second enzymic reaction in which it is converted to ATP. This ATP, described as the "facilitator", feeds back to the beginning of the cycle. Ultimately, the second enzymic reaction gives rise to a detectable product. The "activator" is defined as a substance which is required for an enzymic reaction to take place if all other components needed for that enzymic reaction are present.

P. D. Mize et al., Analytical Biochemistry, 179, 229-235, (1989) describe the use of a masked inhibitor of carboxylesterase. Dephosphorylation, by the action of alkaline phosphatase, unmasks the inhibitor and regenerates the enzyme activity of the carboxylesterase.

DESCRIPTION OF THE PREFERRED EMBODIMENTS

Figure 1:
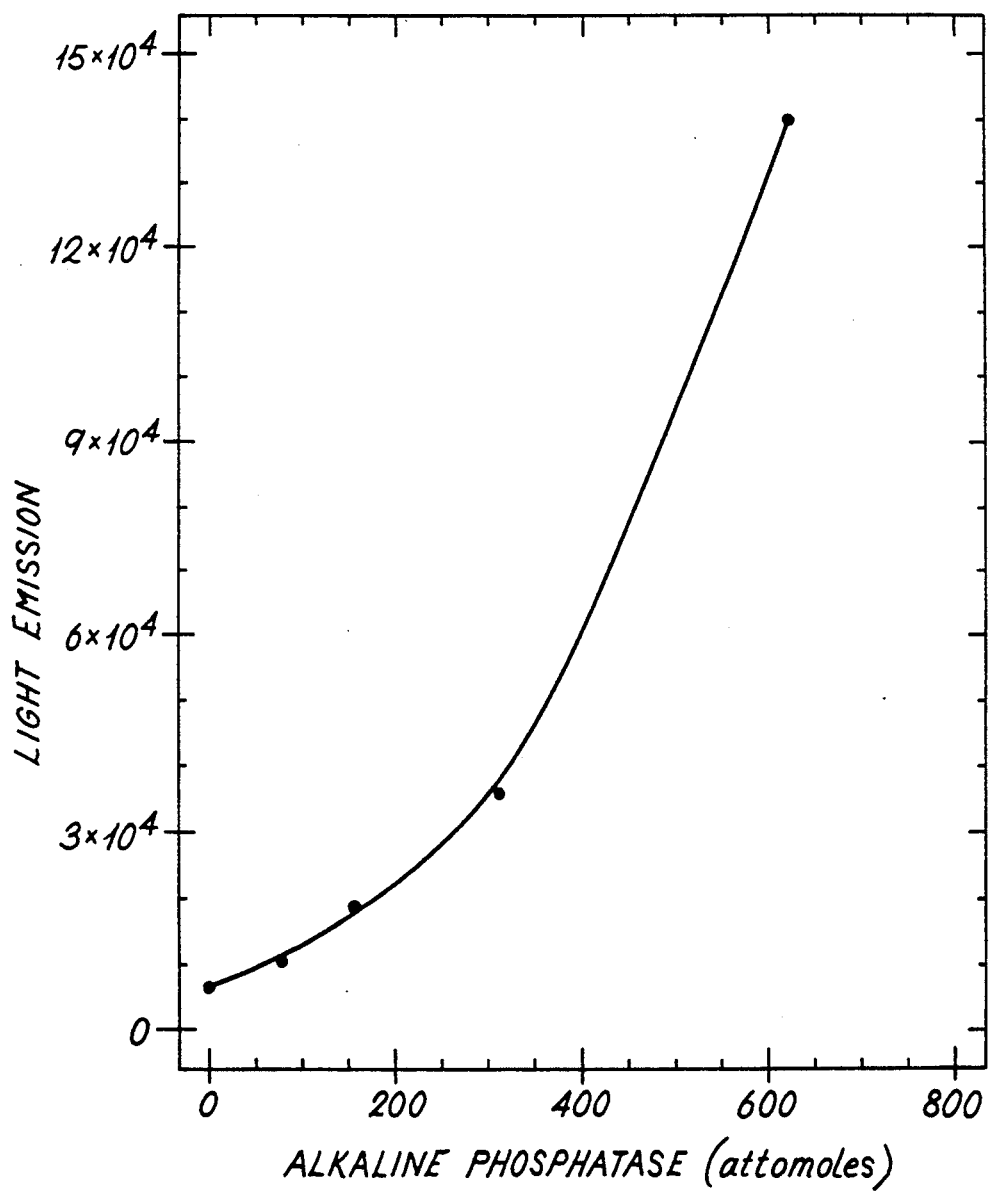
FIG. 1 (see Example 2) shows a standard curve for the assay of alkaline phosphatase by the method of the invention, using a pro-enhancer.

Enhanced chemiluminescent assays are fully described in the above-mentioned prior patent specifications. The reagents, concentrations thereof, incubation conditions and other assay conditions mentioned therein are applicable, *mutatis mutandis*, to the present invention and are herein incorporated by reference.

The reaction can be illustrated as follows, using preferred reagents:

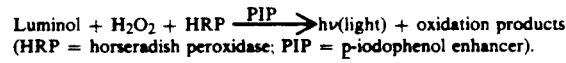

(HRP = horseradish peroxidase; PIP = p-iodophenol enhancer).

The chemiluminescent assays are described as "enhanced" in the sense that the total light emission of the reaction and/or the signal/background ratio is greater than that obtained in the same reaction carried out in the absence of an enhancer. The mechanism of enhancement is not completely understood, but the above prior specifications identify a large number of enhancers. Particularly preferred are p-iodophenol, p-hydroxycinnamic acid and p-imidazol-l-ylphenol. Other examples are p-bromophenol, p-phenylphenol, 2-naphthol, 6-bromo-2-naphthol and 6-hydroxybenzothiazole.

In the present invention, a pro-enhancer or pro-anti-enhancer is used. It will be appreciated that these are relative terms. The difference in enhancement between the pro-enhancer and the enhancer is the crucial necessity. A small degree of enhancement effect of the pro-enhancer is permissible, so long as the contrast in enhancement achieved with pro-enhancer and enhancer is reasonably great. Likewise the pro-anti-enhancer need not be totally inhibitory to enhancement, so long as the difference in inhibition of enhancement achieved using the pro-anti-enhancer and the anti-enhancer is sufficiently great. Normally, it is preferable to arrange that the pro-compound has zero or an insignificant or insubstantial effect on enhancement or inhibition of enhancement, respectively. The pro-compound is preferably a phosphate, which is cleaved by alkaline phosphatase, enabling this enzyme to be the substance directly assayed. (Of course, a ligand-enzyme conjugate, a ligand competing therewith or a binding partner of the ligand, for example, can then be indirectly assayed, each of these substances being measurable because of its dependence on the enzyme as a label in the assay procedure).

Illustrating the two main embodiments of the invention, the preferred pro-enhancer, para-iodophenol phosphate (PIPP), is cleaved by alkaline phosphatase to give para-iodophenol which is a potent enhancer of the peroxidase-catalysed chemiluminescent DPD—peroxide reaction. PIPP does not act as an enhancer and thus does not provide a chemiluminescent signal above the unenhanced background. In the presence of a limiting amount of alkaline phosphatase, the amount of light emission is dependent on the enzyme activity. This assay may be performed in a stepwise manner, but is preferably carried out in one step, in which all of the assay reagents (PIPP, peroxidase, DPD and peroxide) are mixed with the test sample containing alkaline phosphatase.

Alternatively, the preferred pro-anti-enhancer, para-nitrophenyl phosphate (PNPP), is cleaved by alkaline phosphatase to give para-nitrophenol which is an inhibitor of the para-iodophenol enhanced peroxidase-catalysed chemiluminescent DPD—peroxide reaction. PNPP acts as a weak inhibitor, presumably due to non-enzymatic hydrolysis to para-nitrophenol (R. B. McComb, G. N. Bowers, and S. Posen, Alkaline Phosphatase, Plenum Press, New York, 1979, p. 234), but this is minor compared to the inhibition produced by the enzymatically generated para-nitrophenol. In the presence of a limiting amount of alkaline phosphatase the reduction of light emission (% inhibition) is inversely dependent on the enzyme activity.

The enzyme which acts on the pro-compound is conveniently called the "generating enzyme" for the purposes of this specification.

Although the invention is of particular interest in relation to alkaline phosphatase as the generating enzyme, this being an enzyme of particular interest in enzyme immunoassay, it can also be used in relation to a variety of other enzymes. For example, a substituted phenol enhancer can be generated from its $\beta$-D-galactopyranoside by $\beta$-D-galactosidase, its glucopyranoside by $\beta$-D-glucosidase, its sulfate by an aryl sulfatase, or its carboxylate ester by a carboxyesterase. More complex derivatives such as the lacto-N-bioside, i.e. 2-acetamido-2-deoxy-3-0-$\beta$-D-galactopryanosyl-$\beta$-D-glucopyranoside, which is cleavable by fucosyl transferase and the N-acetyl-$\beta$-D-glucosaminide, cleavable by N-acetylglucosaminidase ("NAG") can also be used.

Although it is not a primary intention to use a peroxidase as the generating enzyme, this is possible and is within the scope of the invention. In the chemiluminescent reaction an ordinary peroxidase, preferably basic horseradish peroxidase, such as Sigma Type VI is intended. A peroxidase isoenzyme, e.g. an acidic horseradish peroxidase such as Sigma Type VII, can be used as the generating enzyme.

Certain p-nitrophenol derivatives cleavable by enzymes have been used as substrates for enzymic reactions, yielding p-nitrophenol (a chromogen). Certain phenols are anti-enhancers such as o-methoxyphenol, p-methoxyphenol and 4-hydroxy-3-methoxycinnamic acids. The phosphates, galactosides etc. of these compounds are pro-anti-enhancers cleavable by enzymes to yield the anti-enhancers. There are, therefore, several commercially available derivatives for use as pro-anti-enhancers in the invention.

While the most successful enhancers hitherto have been phenolic compounds (substituted phenols and naphthols), amines can also be used. Generally, N-methylated amines will be suitable pro-enhancers. For example, N-methyl-p-anisidine can be chemically altered, predominantly demethylated, by a peroxidase acidic isoenzyme (which, as explained above, differs from ordinary peroxidases) or by cytochrome P-450. Although the reaction by which the pro-compound is acted on by the enzyme is usually one of cleavage, other kinds of reaction are envisaged, e.g. the reaction of phenol with an iodinase enzyme to para-iodophenol or the reaction of N,N-dimethylaniline to give N,N',N,N'-tetramethylbenzidine in the presence of a demethylating enzyme mentioned above.

N-methyl-para-anisidine does not enhance the said chemiluminescent reaction of DPD, oxidant and peroxidase to a meaningful extent. It has now been found that when N-methyl-p-anisidine is acted on by a horseradish peroxidase acidic isoenzyme, the resulting product, which includes p-anisidine, acts as an enhancer for the said chemiluminescent reaction. The chemiluminescent reaction occurs only weakly in the presence of a peroxidase acidic isoenzyme. However, such an acidic isoenzyme can be used as generating enzyme and thus as a label for an appropriate ligand and, because it catalyses reaction of the pro-enhancer N-methyl-p-anisidine to an enhancer, it can be detected by the assay of the invention.

The generating enzyme should be used in a limiting concentration, relative to that of the pro-enhancer or pro-anti-enhancer, so that the enhancement of light emission (or reduction of enhancement) depends on the production of enhancer molecules by enzymatic catalysis. Obviously, if the enzyme were present in an excess, the required dependence would not be established. The emission of light (or its reduction) is not necessarily directly proportional to the concentration of enzyme present at all concentrations. It may be necessary to establish standard curves for any particular enzyme.

Enhancement of the HRP-catalyzed luminol-peroxide reaction by phenols, naphthols, amines and benzothiazoles has a characteristic concentration dependence. A small amount of enhancer produces a large enhancement of light emission but at higher concentrations of enhancer the enhancement is decreased. Typical examples of this concentration dependence have been disclosed as follows: para-iodophenol, G. H. G. Thorpe et al. Clinical Chemistry 31, 1335–1341 (1985) and 6-hydroxybenzothiazole, G. H. G. Thorpe et al., Analytical Biochemistry 145 96–100 (1985).

The enzyme can be pre-incubated with the pro-enhancer or pro-anti-enhancer, but it is preferred to add the enzyme to the chemiluminescent reactants and pro-enhancer (or enhancer plus pro-anti-enhancer), so that a one step procedure is used.

The light emission is preferably read after a period of 10 to 30 minutes using a photomultiplier tube. However, the reaction produces a glow which can be photographed, if desired.

The phenol-enhanced chemiluminescent reaction as described in U.S. Pat. No. 4,598,044 and British Patent Application 2205945A, was originally optimised for the detection of peroxidase. The pro-enhancer-based assays of this invention require the detection of the enhancer and so initially the reaction was reoptimised for the detection of the enhancer para-iodophenol. A matrix optimisation experiment (sodium luminol 1.25 mmole/l-12.5 $\mu$mole/l, peroxide 2.7 mmole/l-27 $\mu$mole/l, peroxidase 10 ng-1 pg, pH 8.6) showed that an assay mixture containing sodium luminol 42 $\mu$mole/l, peroxide 2 mmole/l, and peroxidase 1 ng in 0.01 mole/l Tris buffer, pH 8.6, gave the best compromise between sensitivity and the dynamic range of the luminometer. Under these conditions the assay for para-iodophenol was linear in the range 4 t picomoles–4.5 femtomoles. The detection limit, based on a signal twice the blank, was 1.2 femtomoles.

In a "on-tube assay" protocol in which the sample, pro-enhancer and the enhanced chemiluminescent reagents were incubated simultaneously, the concentration of PIPP substrate was investigated at several concentrations (15.5 mmole/l–33 mole/l) and a value of 3.3 mmole/l (final concentration 0.33 mmole/l) was considered optimal based on the signal to noise ratio. The response of the assay took the form of a curve such as in FIG. 1. The detection limit based on a signal twice the blank was 100 attomoles.

The invention is particularly applicable to sandwich and competitive ELISAs and for the measurement of any chemical or biological substance which participates in a specific binding interaction, determinable with the aid of an enzyme label.

The following Examples illustrate the invention. Throughout, the phosphates are in the form of their disodium salts and luminol as its sodium salt. The light emissions throughout are in arbitary units.

EXAMPLE 1

Synthesis of para-iodophenyl phosphate (PIPP)

Under argon, p-iodophenol (Aldrich, 12.0 mmol) was dissolved in dry THF (25 ml) containing triethylamine (12.9 mmol). Upon cooling in an ice bath, 2-chloro-2-oxo-1,3,2-dioxaphospholane (Fluka, Chemical Co. Hauppage, N.Y., USA, 13.0 mmol) was added via syringe. The suspension was warmed to room temperature and stirred for 4 hours. The solvent was removed on the rotary evaporator and the paste was treated with anhydrous diethyl ether (90 ml). Filtration under argon and concentration of the filtrate afforded an oil which subsequently solidified. The crude phospholane was ring-opened with NaCN (14.0 mmol) in dry DMF (12 ml) by stirring the components at room temperature for 24 hours. After removal of the solvent in vacuo and trituration of the residue with anhydrous ether, the gummy 2-cyanoethylphosphate diester was beta-eliminated to the monoester by stirring with 7M NH$_4$OH (21 ml) for 24 hours at 45° C. The solution was concentrated to a moist residue, redissolved in absolute ethanol and treated with 25% sodium methoxide in methanol (Aldrich, 12.0 mmol). Azeotropic removal of water was accomplished with several evaporation cycles of anhydrous ethanol. The title compound, as the disodium salt, was then precipitated with acetone and isolated by filtration as a white solid (hydrate) in good yield.

$^1$H NMR (400 mHz, D$_2$O, TMS as external reference): $\delta$4.65 (s, HOD): $\delta$6.83 (d, 2H): $\delta$7.50 (d, 2H). IR (cm$^{-1}$) 1240 (P=0) 1120 and 1000 (P-O-C aromatic), 1000 and 820 (para-substituted benzene ring).

EXAMPLE 2

Assay of alkaline phosphatase based on the release of the enhancer para-iodophenyl (PIP) from its phosphate (PIPP) (pro-enhancer)

A 10 μl sample containing alkaline phosphatase (bovine, 1260 units/mg. protein; Sigma) was added to an assay tube containing 10 μl of PIPP (0.1 mg/ml in 0.1 mol/l, pH 8.6 Tris buffer) and 100 μl of luminol-HRP-peroxide reagent. The luminol-HRP-peroxide reagent was prepared as follows; sodium luminol (12.5 mg) was dissolved in 50 ml Tris buffer (0.1 mol/l, pH 8.6). A 3 ml aliquot was mixed with 2 μl of hydrogen peroxide (30% v/v) and this mixture diluted 1:30 in the Tris buffer. 100 μl HRP (1:50,000 dilution of a 1 mg/ml stock in the Tris buffer) and 1 ml of the 1:30 dilution of luminol-peroxide were mixed together to give the final luminol-HRP-peroxide assay reagent. The assay mixture was incubated at room temperature for an hour and the light intensity measured at intervals using a luminometer (LB 9500, Berthold Laboratories, Nashua, N.H.). A "blank", i.e. luminol, peroxide, peroxidase and PIPP, was also measured. The results are shown in Table 1 below.

TABLE 1

| Incubation time (minutes) | Light emission | |
|---|---|---|
| | Blank | With alkaline phosphatase |
| 5 | 7358 | 17845 |
| 10 | 6770 | 26926 |
| 15 | 5782 | 35250 |
| 30 | 6096 | 50694 |
| 60 | 6427 | 35810 |

Using the above procedure and various dilutions of the alkaline phosphatase, a standard curve (FIG. 1) was obtained for the assay of alkaline phosphatase, in which light emission on the ordinate in arbitrary units (counts/10 seconds) is plotted against concentration of alkaline phosphatase in attomoles. Attomolar amounts of the enzyme were detected.

The PIPP substrate was stable under the conditions of the assay. The blank run in which PIPP was present, but the alkaline phosphatase omitted, showed non-enzymatic hydrolysis to be minimal.

EXAMPLE 3

Assay of alkaline phosphatase based on the release of the anti-enhancer p-nitrophenol (PNP) from its phosphate (PNPP) (pro-anti-enhancer)

In preliminary experiments it was shown that PNP at a concentration of 280 nanomoles/liter in the chemiluminescent reaction mixture inhibited over 90% of the emission. At 1.4 μmole/liter, 98% inhibition was achieved.

Figure 2:
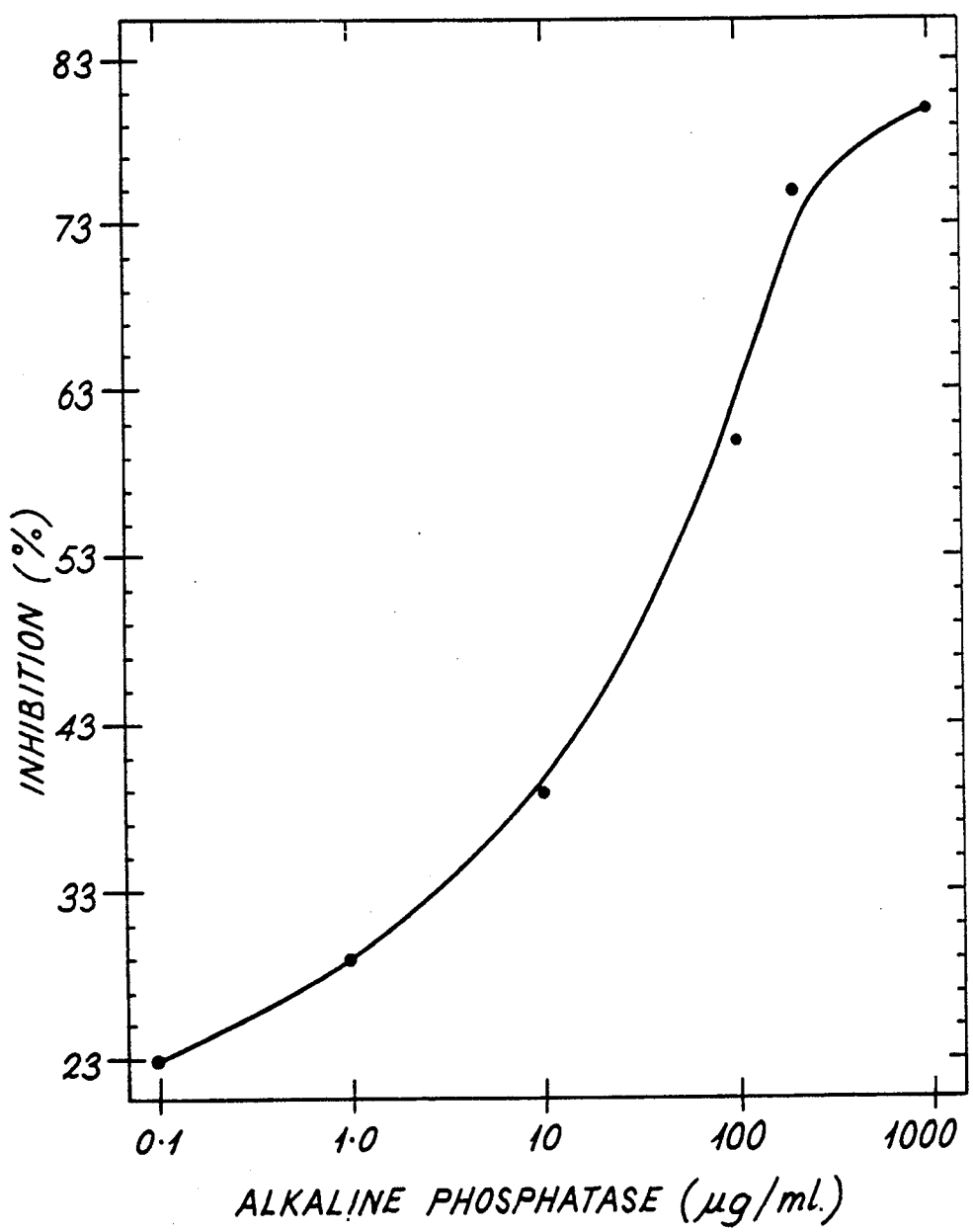
FIG. 2 (see Example 3) shows a standard curve for the assay of alkaline phosphatase by the method of the invention, using an enhancer and a pro-anti-enhancer.

10 μl samples of various dilutions of a stock alkaline phosphatase (1 mg/ml in Tris-MgCl$_2$ buffer) were added to 100 μl of the luminol-HRP-peroxide PIP assay reagent containing PNPP (0.12 mg/ml) to provide a PNPP concentration of about 3.2 millimoles/liter and the light emission measured after 2 minutes. The kinetics of the reaction are shown in Table 2 below. It will be seen that the reduction in light emission occurred rapidly and depended on the concentration of alkaline phosphatase. FIG. 2 shows a standard curve for the assay of alkaline phosphatase in which percentage inhibition on the ordinate is plotted against alkaline phosphatase concentration in μg/ml. on the abscissa.

The percentage inhibition is determined as $$\frac{(A - B) \times 100}{A}, \text{ where}$$

A = signal from the enhanced reaction, i.e. as B but in the absence of alkaline phosphatase and
B = signal from the inhibited reaction.

TABLE 2

| Incubation time (minutes) | Light emission Alkaline phosphatase concentration | | |
|---|---|---|---|
| | Zero (Control) | 1 μg/ml. | 1 mg/ml. |
| 0 | 0 | 0 | 0 |
| 1 | 44 | 31 | 9.5 |
| 2 | 43.5 | 31 | 10 |

EXAMPLE 4

Assay of alkaline phosphatase-biotin conjugate

10 µl samples of various dilutions of an alkaline phosphatase-biotin conjugate (750 units/ml, 6.2 moles biotin/mole protein, Sigma) were assayed using PIPP as described in Example 2. The results are shown in Table 3 below.

TABLE 3

| Concentration of alkaline phosphatase (attomoles) | Light emission | | | |
|---|---|---|---|---|
| | Ex. 4 (Biotin conjug.) | Ex. 5 (PEG conjug.) | Ex. 6 (Anti-IgG conjug.) | Ex. 7 (Immob. on agarose) |
| 0 | 1486 | 9536 | 9536 | 2205 |
| 38 | 4891 | omitted | omitted | 6428 |
| 388 | 7245 | 18878 | 26447 | 8824 |
| 775 | 12720 | 19491 | 46003 | 77535 |
| 1550 | 137104 | 102503 | 96701 | 159312 |
| 3100 | 273578 | 386415 | 280996 | 268185 |

EXAMPLE 5

Assay of alkaline phosphatase-polyethylene glycol conjugate

10 µl samples of various dilutions of an alkaline phosphatase-polyethylene glycol conjugate (98 units/ml, Sigma) were assayed using PIPP as described in Example 2. The results are shown in Table 3 above.

EXAMPLE 6

Assay of alkaline phosphatase-antibody conjugate

10 µl samples of dilutions of an alkaline phosphatase-goat anti human IgG antibody conjugate (0.53 mg/ml, Sigma) were assayed using PIPP as described in Example 2. The results are shown in Table 3 above.

EXAMPLE 7

Assay of alkaline phosphatase immobilized on agarose

10 µl samples of various dilutions of a suspension of an alkaline phosphatase-agarose preparation (4900 units/ml, Sigma) were assayed using PIPP as described in Example 2. The results are shown in Table 3 above.

EXAMPLE 8

Assay of alkaline phosphatase using perborate as the oxidant in the chemiluminescent reaction 10 µl samples of various dilutions of alkaline phosphatase were assayed using PIPP, as described in Example 2, except that the peroxide was replaced by sodium perborate (2 mol/l, Aldrich).

Table 4 shows the results.

TABLE 4

| Concentration of alkaline phosphatase (attomoles) | Light emission | |
|---|---|---|
| | Ex. 8 (Perborate) | Ex. 9 (Isoluminol) |
| 0 | 2563 | 915 |
| 620 | 5816 | 1803 |
| 1240 | 11281 | 2124 |
| 2480 | 32688 | 5691 |

EXAMPLE 9

Assay of alkaline phosphatase using isoluminol as the chemiluminescent reactant

10 µl samples of various dilutions of alkaline phosphatase were assayed using PIPP, as described in Example 2, except that the DPD was replaced by isoluminol (Sigma). The assay mixture was prepared by mixing 3 ml isoluminol (240 mg/l in the Tris buffer), 2 µl hydrogen peroxide (30% v/v) and 30 µl of the 1:50,000 dilution of peroxidase. This isoluminol solution was not further diluted, because the resultant light levels were already low. (This is consistent with the known difference in light emission of isoluminol compared with luminol).

Table 4 above shows the results.

EXAMPLE 10

Chemiluminescent enzyme immunoassay for alpha fetoprotein

The Hybritech Tandem enzyme immunoassay (EIA) for alpha fetoprotein (AFP) (Hybritech, San Diego, Calif.) was used to measure the AFP concentration in a series of standards and serum specimens. The assay is based on an anti-AFP antibody immobilized on polystyrene beads and an alkaline phosphatase-anti-AFP conjugate. The EIA was performed according to the manufacturer's instructions. All assays were performed in duplicate and the bound conjugate measured chemiluminescently. For the chemiluminescent assay, the beads were agitated at room temperature in a tube containing 20 µl of PIPP and 200 µl of luminol-HRP-peroxide (see Example 2) for 30 minutes and then the light intensity measured.

Table 5 shows the results. The signal/background ratio is calculated as the ratio of light emission in the assay and in the same chemiluminescent reaction except that no alkaline phosphatase conjugate is present.

TABLE 5

| Concentration of AFP (ng./ml.) | Signal/background ratio |
|---|---|
| 0 | 1 |
| 25 | 8.8 |
| 88 | 13.7 |
| 237 | 18 |

EXAMPLE 11

Assay for alkaline phosphatase based on the release of the enhancer 2-naphthol from 2-naphthylphosphate 10 µl samples containing various dilutions of alkaline phosphatase (Sigma) were added to an assay tube containing 10 µl of 2-naphthylphosphate (Aldrich, 0.1 mg/ml in 0.1 mol/l, pH 8.6 Tris buffer) and 100 µl of luminol-HRP-peroxide reagent. The assay tube was incubated at room temperature for 30 minutes and the light intensity measured using a luminometer (LB 9500, Berthold Laboratories, Nashua, N.H., USA).

The results are shown in Table 6. Attomolar amounts of the enzyme could be detected.

At high concentrations of alkaline phosphatase, light emission was reduced and this is in accord with the known effect of high concentrations of enhancer on the chemiluminescent reaction.

TABLE 6

| Concentration of alkaline phosphatase (attamoles) | Light emission |
| --- | --- |
| 77.5 | 475 |
| 155 | 7208 |
| 310 | 14100 |
| 620 | 16221 |
| 1240 | 12661 |
| 2480 | 13558 |
| 9920 | 0 |

EXAMPLE 12

Assay for beta-D-galactosidase based on the release of the enhancer 6-bromo-2-naphthol from 6-bromo-2-naphthyl-beta-D-galactopyranoside 10 µl samples containing various dilutions of beta-D-galactosidase (Sigma, 22 mg/ml, 900 U/mg protein) were added to an assay tube containing 10 µl of 6-bromo-2-naphthyl-beta-D-galactopyranoside (Aldrich, saturated solution ca. 0.1 mg/ml in 0.1 mol/l, pH 8.6 Tris buffer) and 100 µl of luminol-HRP-peroxide reagent. The assay tube was incubated and the light intensity measured as in Example 11, with the results shown in Table 7. Attomolar amounts of the enzyme could be detected.

At high concentrations of the enzyme light emission was reduced and this is in accord with the known effect of high concentrations of enhancer on the luminescent reaction.

TABLE 7

| Concentration of $\beta$-galactosidase (attomoles) | Light emission |
| --- | --- |
| 80 | 8933 |
| 400 | 7502 |
| 800 | 14037 |
| 4,000 | 24368 |
| 40,000 | 0 |

EXAMPLE 13

Assay for beta-D-glucosidase based on the release of the enhancer 6-bromo-2-naphthol from 6-bromo-2-naphthyl-glucopyranoside 10 µl samples containing various dilutions of beta-D-glucosidase (Sigma, 4.8 units/mg) were added to an assay tube containing 10 µl of 6-bromo-2-naphthyl-glucopyranoside (Aldrich, 10 ng/ml in 0.1 mol/l, pH 8.6 Tris buffer) and 100 µl of luminol-HRP-peroxide reagent. The assay tube was incubated and the light intensity measured as in Example 11, with the results shown in Table 8.

TABLE 8

| Concentration of $\beta$-glucosidase (picomoles) | Light emission |
| --- | --- |
| 0.014 | 0 |
| 0.14 | 407 |
| 1.4 | 1725 |
| 14 | 4582 |
| 1460 | 138319 |

EXAMPLE 14

Assay for arylsulfatases based on the release of the enhancer 2-naphthol from 2-naphthyl sulfate 100 µl samples containing various dilutions of arylsulfatase (Sigma, 12 units/mg) were added to an assay tube containing 100 µl of 2-naphthyl sulfate (Aldrich, 0.1 mg/ml in 10 mmol/l, pH 5 acetate buffer). After a 30-minute incubation, 10 µl of the mixture was removed and added to 100 µl of luminol-HRP-peroxide reagent. The assay tube was incubated at room temperature for 30 minutes and the light intensity measured as in Example 11, with the results shown in Table 9.

TABLE 9

| Concentration of aryl sulfatase (ng./ml.) | Light emission |
| --- | --- |
| 1 | 59 |
| 10 | 329 |
| 100 | 870 |
| 1,000 | 1032 |
| 100,000 | 999 |

EXAMPLE 15

Assay for horseradish peroxidase (acidic isoenzyme) based on formation of an enhancer from N-methyl-para-anisidine The acidic isoenzymes of peroxidase (Type VII and VIII), in the presence of peroxide or molecular oxygen, catalysed a reaction of the proenhancer N-methyl-para-anisidine to form products which enhanced the luminol-HRP(basic isoenzyme)-peroxide reaction. A 50 µl sample containing type VII horseradish peroxidase isoenzyme (117 units/mg protein RZ=3.7, Sigma) or the Type VIII horseradish peroxidase isoenzyme (100 units/mg protein RZ=3.4, Sigma) in 0.1 mole/l phosphate buffer, pH 5.5, was incubated for 10 minutes at room temperature with 50 µl of N-methyl-para-anisidine (0.01 mg/ml) in the same phosphate buffer. A 10 µl sample was then removed and added to 100 µl of the sodium luminol-HRP-peroxide reagent. The mixture was incubated at room temperature for 5-30 minutes and the light intensity measured. The assay was also performed using phosphate buffer containing hydrogen peroxide (50 mmole/l). The dose-response relationship obtained is illustrated for the Type VII acidic HRP isoenzyme in Table 10 below.

TABLE 10

| HRP VII (pg) | Light emission | Signal/blank |
| --- | --- | --- |
| 0 | 2109 | 1 |
| 5000 | off scale | — |
| 500 | 266238 | 126 |
| 50 | 24788 | 11.7 |
| 5 | 4319 | 2.0 |
| 1 | 2176 | 1.0 |

The detection limit for the type VII acidic isoenzyme was 5 picograms = $5 \times 10^{-12}$ grams = approx. 125 attomoles (signal = twice assay blank; assumed molecular weight of the peroxidase = 40,000).

Silica gel chromatography (Analtech Inc., Newark, N.J.) was used to assess the reaction of solutions of N-methyl para-anisidine and para-anisidine with Type VII acidic horseradish peroxidase. The plates were developed in hexane: ethyl acetate (88:12 v/v) and examined under ultra-violet light. Thin layer chromatography of solutions of N-methyl-para-anisidine which had been treated with Type VII acidic isoenzyme, showed that the proenhancer was converted into the same product obtained when para-anisidine (the initial N-demethylation product) was reacted similarly. A further TLC experiment correlated the products obtained with dilution of the isoenzyme, Thus, a solution of N-methyl-para-anisidine (1.0 mg/ml) in phosphate buffer (0.1 mole/l, pH 5.5) was incubated with dilutions of Type VII peroxidase and then the reaction mixture (25/μl) chromatographed on a reverse phase TLC plate (Si-C$_{18}$, Baker Chemical Co., Phillipsburg, N.J.). Development was as described above and the resolved components were visualised by exposure to iodine vapour for 30 minutes. The results are shown in Table 11 below, the + symbol denoting the appearance of a spot. In some experiments there were faint spots ascribed to other products.

TABLE 11

| Type VII Dilution | Spot ascribed to products of: | |
|---|---|---|
| | Pro-enhancer (Rf 0.52) | Enhancer (Rf 0.24) |
| 1:2,000 | − | +++ |
| 1:3,000 | − | +++ |
| 1:50,000 | ++ | + |
| 1:100,000 | +++ | − |
| 1:1,000,000 | +++ | − |

It is desirable to purify the N-methyl-para-anisidine and this can be done as follows.

N-methyl-para-anisidine (500 mg) was dissolved in DMSO (250 μl) and then diluted with ethanol (5 ml). This solution was mixed with "Norit" activated charcoal (American Norit Co. Inc., Jacksonville, Fla.) (25 mg) and refluxed for 10 minutes. Ice cold distilled water (3 ml) was added to the filtrate and the mixture allowed to stand overnight at 4° C. The precipitate of N-methyl-para-anisidine was recovered by filtration.

I claim:

1. A method of determining the presence or amount of an enzyme comprising the steps of:
  subjecting a peroxidase, an oxidant and a dihydrophthalazinedione (DPD) to a chemiluminescent reaction in the presence of a pro-enhancer and a sample suspected of containing said enzyme, said enzyme acting catalytically to cleave the pro-enhancer to generate an enhancer of the chemiluminescent reaction, said enzyme being present in a limiting concentration relative to that of the pro-enhancer so that the enhancement depends on said generation of the enhancer by said enzymatic catalysis;
  detecting or measuring the resulting chemiluminescence; and
  relating the presence or amount of said chemiluminescence to the presence or amount of said enzyme.

2. A method according to claim 1, wherein the reaction mixture of the peroxidase, oxidant, DPD and the pro-enhancer is formed and the enzyme is added to said mixture without prior incubation with the pro-enhancer.

3. A method according to claim 1, wherein the pro-enhancer is cleavable to produce a para-iodophenol, para-hydroxycinnamic acid or para-imidazol-1-ylphenol enhancer.

4. A method according to claim 1, wherein a phosphate pro-enhancer is cleaved by alkaline phosphatase, which is assayed.

5. A method according to claim 1, wherein the peroxidase is horseradish peroxidase, the oxidant is hydrogen peroxide and the DPD is luminol.

6. A method of determining the presence or amount of an enzyme comprising the steps of:
  subjecting a peroxidase, an oxidant and a dihydrophthalazinedione (DPD) to a chemiluminescent reaction in the presence of (1) an enhancer of the chemiluminescent reaction, (2) a pro-anti-enhancer and (3) a sample suspected of containing said enzyme, said enzyme acting catalytically to cleave the pro-anti-enhancer to generate an anti-enhancer which at least partly inhibits the enhancement, said enzyme being present in a limiting concentration relative to that of the pro-anti-enhancer so that the inhibition of enhancement depends on said generation of the anti-enhancer by said enzymatic catalysis;
  detecting or measuring the resulting chemiluminescence; and
  relating the presence or amount of said chemiluminescence to the presence or amount of said enzyme.

7. A method according to claim 6, wherein a reaction mixture of the peroxidase, oxidant, DPD, enhancer and pro-anti-enhancer is formed and the enzyme is added to said mixture without prior incubation with the pro-anti-enhancer.

8. A method according to claim 6, wherein the peroxidase is horseradish peroxidase, the oxidant is hydrogen peroxide and the DPD is luminol.

9. A method according to claim 8, wherein the pro-anti-enhancer is para-nitrophenol phosphate.

10. A kit suitable for carrying out an assay in which a chemiluminescent reaction takes place between a peroxidase, an oxidant and a dihydrophthalazinedione (DPD), in the presence of an enhancer of the chemiluminescent reaction, said kit comprising in separate containers (1) a DPD and (2) a pro-enhancer which is cleavable by an enhancer-generating enzyme to form an enhancer of the chemiluminescent reaction.

11. A kit according to claim 10, which further includes at least one component, each in a separate container, selected from the group consisting of: (1) a conjugate of a ligand bound to said enhancer generating enzyme, (2) a peroxidase and (3) an oxidant.

12. A kit according to claim 10, wherein the pro-enhancer is a phosphate cleavable by alkaline phosphatase to generate said enhancer.

13. A kit according to claim 10, wherein the pro-enhancer is cleavable to produce a para-iodophenol, para-hydroxycinnamic acid or para-imidazol-1-ylphenol enhancer.

14. A kit according to claim 10, wherein the DPD is luminol.

15. A kit suitable for carrying out an assay in which a chemiluminescent reaction takes place between a peroxidase, an oxidant and a dihydrophthalazinedione (DPD), in the presence of an enhancer of the chemiluminescent reaction, said kit comprising in separate containers (1) a DPD and (2) said enhancer and a pro-anti-enhancer which is cleavable by an enzyme to form an anti-enhancer which at least partly inhibits the enhancement.

16. A kit according to claim 15, which further includes at least one component each in a separate container selected from the group consisting of: (1) a conjugate of a ligand bound to said enzyme, (2) a peroxidase and (3) an oxidant.

17. A kit according to claim 15, wherein said pro-anti-enhancer is para-nitrophenol phosphate.

18. In an immunoassay for an analyte utilizing as the detection or measurement system a peroxidase, an oxidant and a dihydrophthalazinedione (DPD) to generate a chemiluminescent reaction comprising reacting analyte, a component which specifically binds to the analyte, and said detection or measurement system for detecting or measuring the presence or amount of an analyte based on the formation of an immune complex, the improvement comprising carrying out the chemiluminescent reaction in the presence of a pro-enhancer and an enzyme label bound to a ligand which contributes to the formation of the immune complex, said enzyme acting catalytically to cleave said pro-enhancer to form an enhancer of the chemiluminescent reaction, said enzyme being present in a limiting concentration relative to that of the pro-enhancer so that the enhancement depends on the generation of the enhancer by said enzymatic catalysis.

19. A method according to claim 18, wherein the reaction mixture of the peroxidase, oxidant, DPD and the pro-enhancer is formed and the enzyme is added to said mixture without prior incubation with the pro-enhancer.

20. A method according to claim 18, wherein the pro-enhancer is cleavable to produce a para-iodophenol, para-hydroxycinnamic acid or para-imidazol-1-ylphenol enhancer.

21. A method according to claim 18, wherein a phosphate pro-enhancer is cleaved by alkaline phosphatase.

22. A method according to claim 18, wherein the peroxidase is horseradish peroxidase, the oxidant is hydrogen peroxide and the DPD is luminol.

23. In an immunoassay for an analyte utilizing as the detection or measurement system a peroxidase, an oxidant, a dihydrophthalazinedione (DPD) and an enhancer to generate a chemiluminescent reaction comprising reacting analyte, a component which specifically binds to the analyte, and said detection or measurement system for detecting or measuring the presence or amount of an analyte based on the formation of an immune complex, the improvement comprising carrying out the chemiluminescent reaction in the presence of a pro-anti-enhancer and an enzyme label bound to a ligand which contributes to the formation of the immune complex, said enzyme acting catalytically to cleave said pro-anti-enhancer to form an anti-enhancer which at least partly inhibits the enhancement of the chemiluminescent reaction, said enzyme being present in a limiting concentration relative to that of the pro-anti-enhancer so that the inhibition of enhancement depends on the generation of the anti-enhancer by said enzymatic catalysis.

24. A method according to claim 23 wherein a reaction mixture of the peroxidase, oxidant, DPD, enhancer and pro-anti-enhancer is formed and the enzyme is added to said mixture without prior incubation with the pro-anti-enhancer.

25. A method according to claim 23, wherein the peroxidase is horseradish peroxidase, the oxidant is hydrogen peroxide and the DPD is luminol.

26. A method according to claim 25, wherein the pro-anti-enhancer is paranitrophenol phosphate.

* * * * *